United States Patent
Ravishankar et al.

(10) Patent No.: US 11,232,344 B2
(45) Date of Patent: Jan. 25, 2022

(54) MULTI-TASK FEATURE SELECTION NEURAL NETWORKS

(71) Applicant: General Electric Company, Schenectady, NY (US)

(72) Inventors: Hariharan Ravishankar, Bangalore (IN); Bharath Ram Sundar, Bangalore (IN); Prasad Sudhakar, Bangalore (IN); Rahul Venkataramani, Bangalore (IN); Vivek Vaidya, Bangalore (IN)

(73) Assignee: General Electric Company, Schenectady, NY (US)

(*) Notice: Subject to any disclaimer, the term of this patent is extended or adjusted under 35 U.S.C. 154(b) by 1088 days.

(21) Appl. No.: 15/799,698

(22) Filed: Oct. 31, 2017

(65) Prior Publication Data
US 2019/0130247 A1 May 2, 2019

(51) Int. Cl.
*G06N 3/04* (2006.01)
*G06N 5/02* (2006.01)
*G16H 50/20* (2018.01)
*G06N 3/08* (2006.01)

(52) U.S. Cl.
CPC ............ *G06N 3/04* (2013.01); *G06N 3/0454* (2013.01); *G06N 3/08* (2013.01); *G06N 5/025* (2013.01); *G16H 50/20* (2018.01)

(58) Field of Classification Search
CPC .......... G06N 3/04; G06N 3/0454; G06N 3/08; G06N 5/025; G16H 50/20
See application file for complete search history.

(56) References Cited

U.S. PATENT DOCUMENTS

| | | | |
|---|---|---|---|
| 9,367,818 B2 | 6/2016 | Dan et al. | |
| 9,477,905 B2 | 10/2016 | Xiaoming et al. | |
| 9,719,842 B2 | 8/2017 | Paradis et al. | |
| 2012/0035856 A1 | 2/2012 | Paradis et al. | |
| 2012/0178100 A1 | 7/2012 | Wagner et al. | |
| 2016/0055420 A1 | 2/2016 | Karanam et al. | |
| 2017/0032035 A1 | 2/2017 | Gao et al. | |
| 2017/0175169 A1 | 6/2017 | Lee et al. | |
| 2017/0209105 A1* | 7/2017 | Fan | A61B 6/5205 |

(Continued)

FOREIGN PATENT DOCUMENTS

| | | |
|---|---|---|
| WO | 2016141282 A1 | 9/2016 |
| WO | 2017053592 A1 | 3/2017 |

OTHER PUBLICATIONS

Riemer et al., "A Deep Learning and Knowledge Transfer Based Architecture for Social Media User Characteristic Determination", Jun. 5, 2015, Proceedings of Social NLP 2015@NAACL-HLT, pp. 39-47 (Year: 2015).*

(Continued)

*Primary Examiner* — Alan Chen
*Assistant Examiner* — Brent Johnston Hoover (57) ABSTRACT

The present approach relates to feature ranking within deep neural networks in a multi-task and/or multi-label setting. Approaches are described to identify features that are task-specific as well as features that are shared across multiple tasks. In addition to facilitating interpretability, the selected subset of features can be used to make efficient models leading to better stability & regularization along with reduced compute and memory.

20 Claims, 6 Drawing Sheets

(56) References Cited

U.S. PATENT DOCUMENTS

2018/0018571 A1* 1/2018 Schwartz ............... G06N 5/02
2018/0276533 A1* 9/2018 Ding .................. G06N 3/08

OTHER PUBLICATIONS

Emrani et al., "Prognosis and Diagnosis of Parkinson's Disease Using Multi-Task Learning", Aug. 17, 2017, KDD 2017 Applied Data Science Paper, pp. 1457-1466 (Year: 2017).*

Romera-Paredes et al., "Exploiting Unrelated Tasks in Multi-Task Learning", 2012, n Proceedings of the 15th International Conference on Artificial Intelligence and Statistics (AISTATS) 2012, La Palma, Canary Islands, pp. 951-959 (Year: 2012).*

Xue et al., "Full Quantification of Left Ventricle via Deep Multitask Learning Network Respecting Intra- and Inter-Task Relatedness", Jun. 14, 2017, arXiv: 1706.01912v2, pp. 1-8 (Year: 2017).*

Liu, Xiaodong, et al.; "Representation Learning Using Multi-Task Deep Neural Networks for Semantic Classification and Information Retrieval" Nara Institute of Science and Technology, 2015, 10 pages, http://www.aclweb.org/anthology/N15-1092.

Li, Yifeng, et al.; "Deep Feature Selection: Theory and Application to Identify Enhancers and Promoters", Centre for Molecular Medicine and Therapeutics, 2017, 13 pages, https://pdfs.semanticscholar.org/ac2ac075773cc936a206c3ebb2339376d586bcbd.pdf.

Shridumar, Avanti, et al.; "Not Just a Black Box: Learning Important Features Through Propagating Activation Differences", Department of Computer Science, Apr. 2017, 6 pages, https://arxiv.org/abs/1605.01713.

Yang, Yongxin, et al.; "Deep Multi-task Representation Learning: A Tensor Factorisation Approach", Queen Mary, University of London, https://arxiv.org/abs/1605.06391, 2017, 12 pages.

Yang, Yongxin, et al.; "Trace Norm Regularised Deep Multi-Task Learning", Queen Mary, University of London, https://arxiv.org/abs/1606.04038, 2017, 4 pages.

Li, Jundong, et al.; "Feature Selection: A Data Perspective", https://arxiv.org/pdf/1601.07996.pdf, 2016, 75 pages.

Caruana, Rich, et al.; "Multitask Learning", School of Computer Science, http://reports-archive.adm.cs.cmu.edu/anon/1997/CMU-CS-97-203.pdf, Sep. 23, 1997, 255 pages.

Zhang, Daoqiang, et al.; "Multi-Modal Multi-Task Learning for Joint Prediction of Multiple Regression and Classification Variables in Alzheimer's Disease", PMC US National Library of Medicine National Institutes of Health, https://www.ncbi.nlm.nih.gov/pmc/articles/PMC3230721/, vol. 62, 2 pages, Oct. 4, 2011.

Ganchev, Philip, et al.; "Transfer Learning of Classification Rules for Biomarker Discovery and Verification from Molecular Profiling Studies", PMC US National Library of Medicine National Institutes of Health, https://www.ncbi.nlm.nih.gov/pmc/articles/PMC3706089/, Jul. 9, 2013, 7 pages.

Emarni, Saba, et al.; "Prognosis and Diagnosis of Parkinson's Disease Using Multi-Task Learning", KDD '17 Proceedings of the 23rd ACM SIGKDD International Conference on Knowledge Discovery and Data Mining, http://dl.acm.org/citation.cfm?id=3098065&dl=ACM&coll=DL&CFID=969929565&CFTOKEN=64529484, pp. 1457-1466, 2017.

* cited by examiner

MULTI-TASK FEATURE SELECTION NEURAL NETWORKS

BACKGROUND

The subject matter disclosed herein relates to feature ranking using neural networks, and in particular to the use of machine learning techniques to facilitate a feature ranking process which may facilitate selection of features of interest.

Deep learning algorithms, such as artificial neural networks, are a learning tool used in a variety of data analysis tasks, such as data classification, regression, de-noising, dimension reduction and so forth. In these contexts, deep learning algorithms have been used successfully on problems from different fields, including speech recognition, computer vision, language translation, and so forth. However, one criticism or drawback of deep neural networks is their lack of interpretability. In particular, traditional machine learning algorithms like logistic regression, decision trees, and so forth produce interpretable models, where it is straightforward to rank the relevance of features for a specific task. In certain problems like anomaly detection in healthcare, it might be beneficial to explain the contributions of various factors towards a prediction, in addition to achieving satisfactory performance on the analytic. Such interpretability is typically not possible conventional applications of an artificial neural network.

BRIEF DESCRIPTION

In one embodiment, feature ranking neural network is provided. In accordance with this embodiment, the feature ranking neural network includes: an input layer, a broadcast layer encoding a plurality of weights, two or more separate and parallel branches of the feature ranking neural network, and an output layer downstream from the branches, wherein the output layer is configured to provide an output of the feature ranking neural network. The plurality of weights comprise a task specific weight for each task of a plurality of tasks for which the neural network is trained. The branches are configured to receive a set of filtered inputs from the broadcast layer based on the weights encoded by the broadcast layer. Each branch corresponds to a different task.

In a further embodiment, a feature ranking method is provided. In accordance with this embodiment, a plurality of input samples is provides as a training data set to an input layer of a neural network. Each input sample is characterized by one or more features. The neural network comprises a broadcast layer comprising a respective weight for each task of a plurality of tasks. The input samples are processed to train the respective weight for each task for each of the one or more features. For one or more tasks of the plurality of task, one or more features are identified as being relevant to a respective task based on the respective weights of the one or more features with respect to the respective tasks.

In an additional embodiment, a method for generating a reduced feature set model is provided. In accordance with this embodiment, one or more weights associated with a broadcast layer of a trained neural network are acquired. Each weight is associated with a respective feature and task combination. One or more task-specific features are identified for a given task based on the weights. A model is generated based on the one or more task-specific features, wherein the one or more task-specific features is a subset of a larger feature set for which the trained neural network was trained.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein.

DETAILED DESCRIPTION

One or more specific embodiments will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

While certain aspects of the following discussion are provided in the context of analysis of medical data, it should be appreciated that the present techniques are not limited to such medical contexts. Indeed, any examples and explanations provided herein in such a medical context is only to facilitate explanation by providing instances of certain real-world implementations and applications. However, the present approaches may also be utilized in other suitable data analysis contexts. In general, the present approaches may be useful in any data analysis context where interpretability of artificial neural network outputs is desired, such as to facilitate selection of one or more features of interest in the relevant analytic context.

With the preceding introductory comments in mind, aspects of the present approaches described herein utilize neural networks in a feature identification or ranking context, with identified features then potentially being selected for a particular application. As used herein, a feature, is a metric used to capture or characterize a phenomenon. Such a feature may be an individual measurable property or characteristic (such as an activity, level, a duration, a binding coefficient, and so forth) of some observed phenomenon, though it is not necessarily an actual measurement and may take other forms, such as a qualitative characterization or observation. Neural networks as discussed herein may encompass deep neural networks, fully connected networks, convolutional neural networks (CNNs), perceptrons, auto encoders, recurrent networks, wavelet filter banks, or other neural network architectures. These techniques are referred to herein as deep learning techniques, though this terminology may also be used specifically in reference to the use of deep neural networks, which is a neural network having a plurality of layers.

As discussed herein, deep learning techniques (which may also be known as deep machine learning, hierarchical learning, or deep structured learning) are a branch of machine learning techniques that employ mathematical representations of data and artificial neural network for learning. By way of example, deep learning approaches may be characterized by their use of one or more algorithms to extract or model high level abstractions of a type of data of interest. This may be accomplished using one or more processing layers, with each layer typically corresponding to a different level of data abstraction and, therefore potentially employing or utilizing different aspects of the initial data or outputs of a preceding layer (i.e., a hierarchy or cascade of layers) as the target of the processes or algorithms of a given layer. In a data analysis context, this may be characterized as different layers corresponding to the different feature levels or levels of abstraction in the data.

In general, the processing from one level or abstraction to the next can be considered as one 'stage' of the analysis process. Each stage of the analysis can be performed by separate neural networks or by different parts of one larger neural network. For example, as discussed herein, a single deep learning network may cover all stages in an analytic process (e.g., from an initial input to an output data set). Alternatively, separate distinct deep learning network(s) may each cover only one stage (or a subset of stages) of the overall analysis process.

As part of the initial training of deep learning processes to solve a particular problem, training data sets may be employed that have known initial values and known or desired values for a final output of the deep learning process. The training of a single stage may have known input values corresponding to one representation space and known output values corresponding to a next-level representation space. In this manner, the deep learning algorithms may process (either in a supervised or guided manner or in an unsupervised or unguided manner) the known or training data sets until the mathematical relationships between the initial data and desired output(s) are discerned and/or the mathematical relationships between the inputs and outputs of each layer are discerned and characterized. Similarly, separate validation data sets may be employed in which both the initial and desired target values are known, but only the initial values are supplied to the trained deep learning algorithms, with the outputs then being compared to the outputs of the deep learning algorithm to validate the prior training and/or to prevent over-training.

Figure 1:
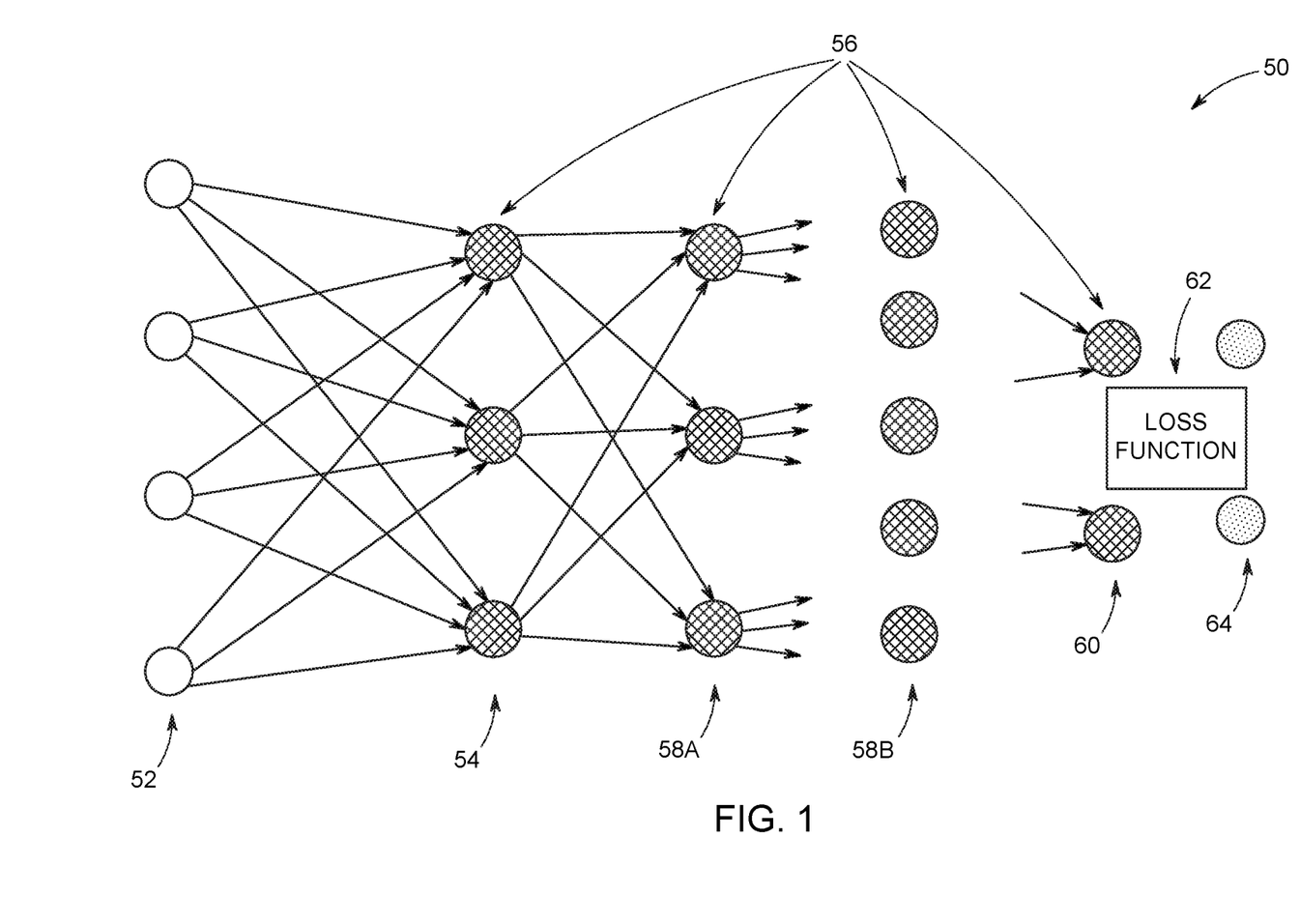
FIG. 1 depicts an example of an artificial neural network for training a deep learning model, in accordance with aspects of the present disclosure.

With the preceding in mind, FIG. 1 schematically depicts an example of an artificial neural network 50 that may be trained as a deep learning model as discussed herein. In this example, the network 50 is multi-layered, with a training input 52 and multiple layers including an input layer 54, hidden layers 58A, 58B, and so forth, and an output layer 60 and the training target 64 present in the network 50. Each layer, in this example, is composed of a plurality of "neurons" or nodes 56. The number of neurons 56 may be constant between layers or, as depicted, may vary from layer to layer. Neurons 56 at each layer generate respective outputs that serve as inputs to the neurons 56 of the next hierarchical layer. In practice, a weighted sum of the inputs with an added bias is computed to "excite" or "activate" each respective neuron of the layers according to an activation function, such as rectified linear unit (ReLU), sigmoid function, hyperbolic tangent function, or otherwise specified or programmed. The outputs of the final layer constitute the network output 60 which, in conjunction with a target value or construct 64, are used to compute some loss or error function 62, which will be backpropagated to guide the network training.

The loss or error function 62 measures the difference between the network output 60 and the training target 64. In certain implementations, the loss function may be a mean squared error (MSE). Alternatively, the loss function 62 could be defined by other metrics associated with the particular task in question, such as a softmax function.

With the preceding in mind, the neural network 50 may be trained for use in the analysis of data in a manner that facilitates ranking or identification of relevant features based on their relevance to a given task(s) and, potentially, selection of some or all of these features for a given application or use. In particular, the present disclosure describes an approach to perform feature ranking and/or selection within deep neural networks in a single-task or multi-task/multi-label setting. Approaches are described to separate out and to discover features that are specific to a single task or limited subset of tasks (e.g., two or three tasks) and others that are shared across multiple or all tasks. Applications of such approaches include, but are not limited to, biomarker discovery and targeted therapy. In addition to gaining interpretability, the identified subset of features can be used to make leaner, and/or more efficient models based solely or primarily on those features identified as being particularly relevant to a given task, leading to better stability & regularization along with reduced computation requirements and/or memory requirements. User inputs may also be employed in both identifying the features most relevant to a given task (such as based on domain knowledge) and/or to select from those features so identified to for subsequent operations, such as formation of a model based on a reduced or limited set of features.

Figure 2:
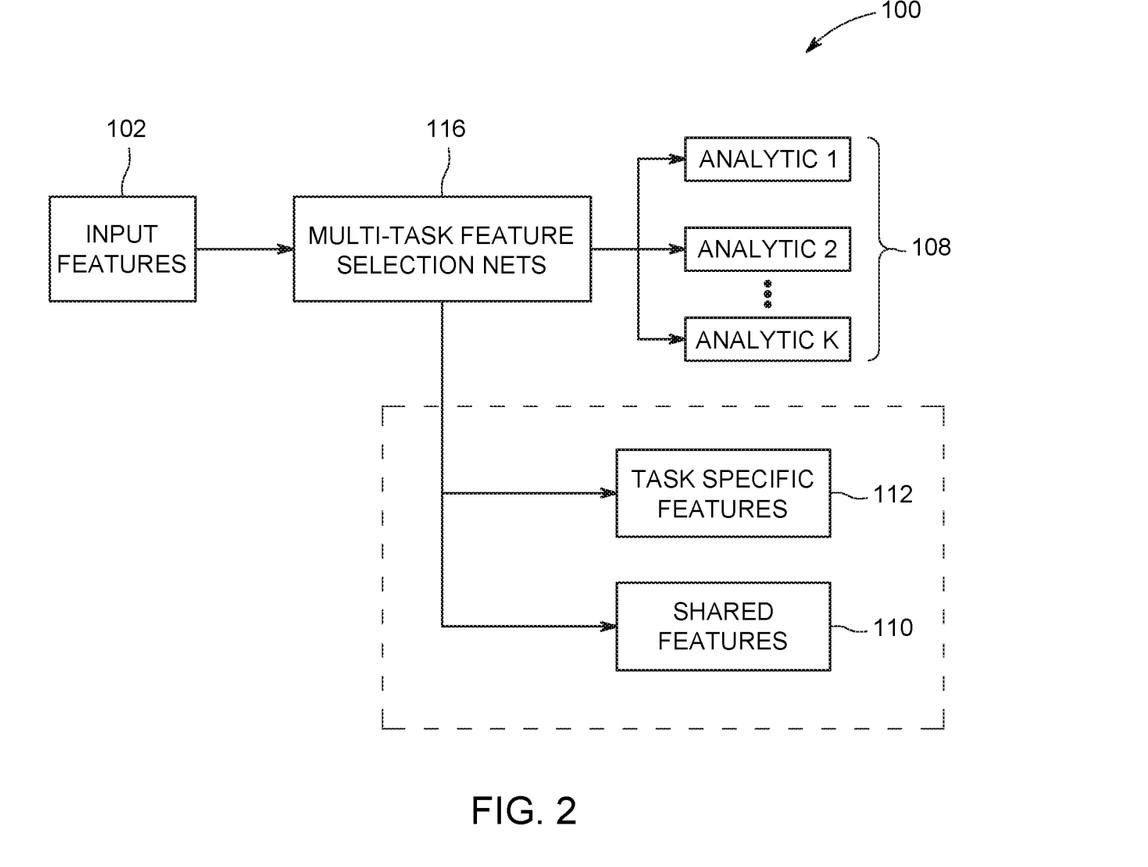
FIG. 2 depicts a multi-task deep learning framework where input samples described by the features can have multiple labels from K tasks, in accordance with aspects of the present disclosure.

FIG. 2 depicts an example of a multi-task deep learning framework 100 where input samples described by one or more features 102 can have multiple labels from K tasks corresponding to analytic results 108 (e.g., predictions). In one implementation, the present approach discovers features that are shared (shared features 110) across many or all of the K tasks 108 and also task-specific features (task specific features 112) that are specific to a single task or a limited number of tasks (e.g., two or three tasks). The specificity of features across certain tasks may be useful in revealing useful patterns or establishing relationships that may lead to better understanding of data and/or tasks and also towards building intelligent systems. In the depicted example, the multi-task feature ranking and/or selection is accomplished using one or more multi-task feature ranking neural networks or parallel branches of a neural network (shown collectively using reference number 116) that perform as a joint feature discovery engine for different tasks 108.

Figure 3:
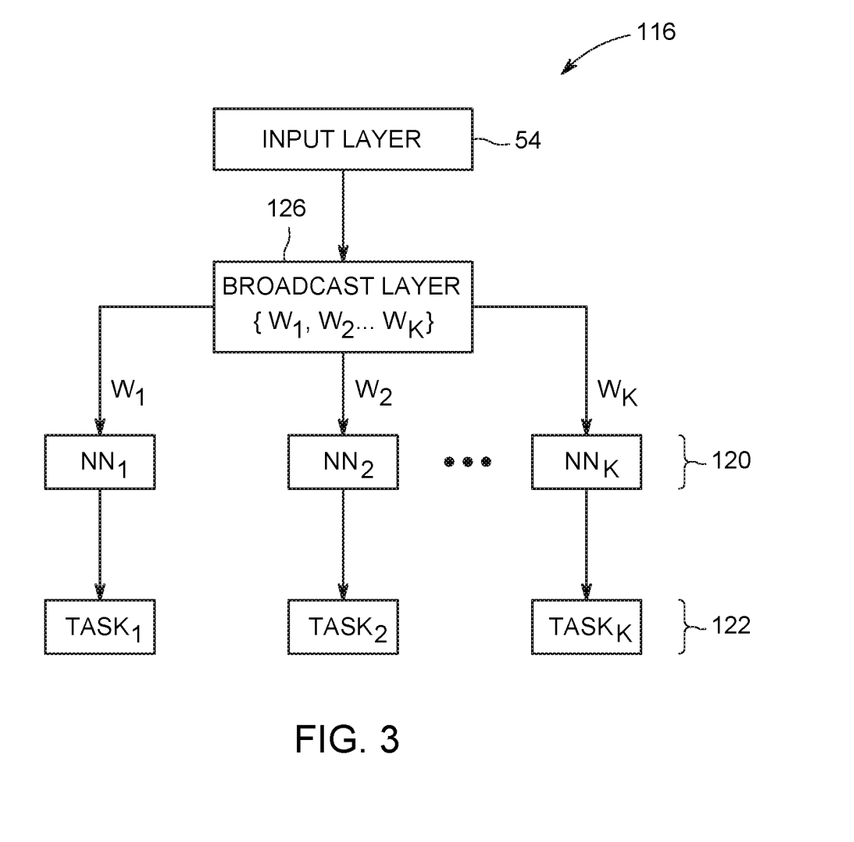
FIG. 3 depicts a multi-task deep learning algorithm where input features are processed by K neural networks for predicting the K tasks, in accordance with aspects of the present disclosure.
Figure 4:
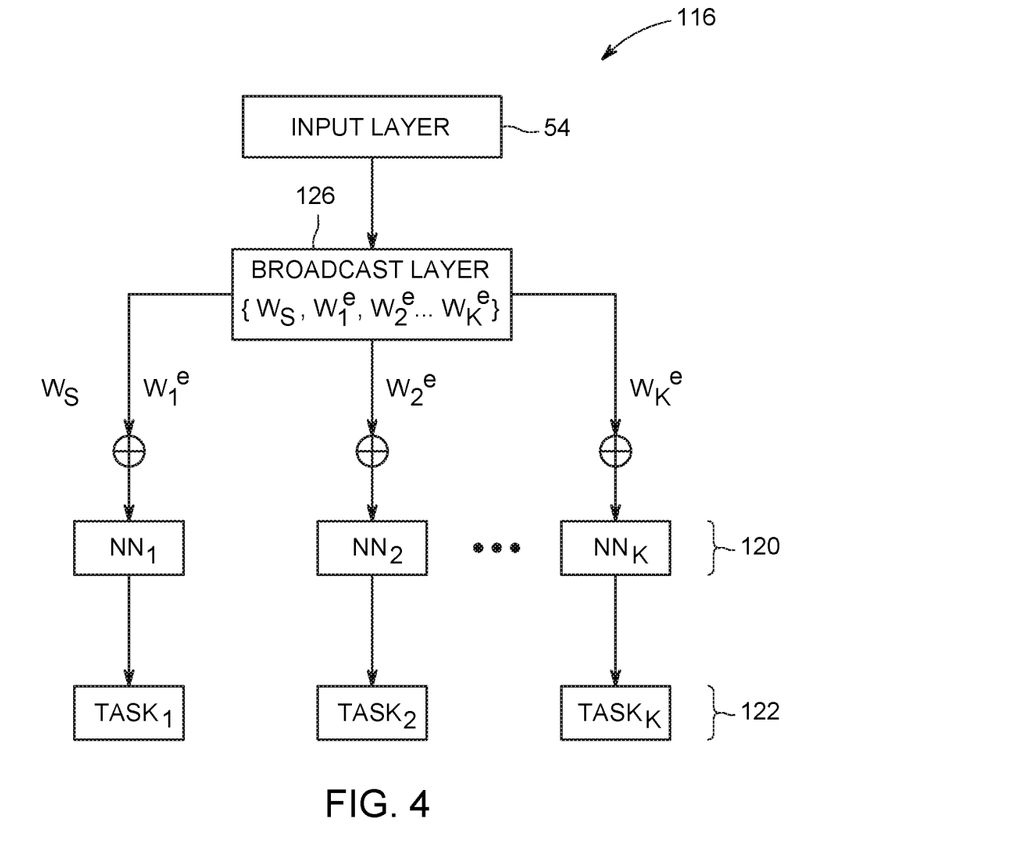
FIG. 4 depicts an alternative representation of a multi-task deep learning algorithm where input features are processed by K neural networks w for predicting the K tasks, in accordance with aspects of the present disclosure.

Turning to FIGS. 3 and 4, an example of multi-task feature ranking network 116 is provided. In this example, the multi-task feature ranking network 116 is in the form of a multi-task deep learning algorithm in which input features 102 (input via input layer 54) are processed by K neural networks or branches 120 of a neural network for predicting the K tasks 122. To facilitate the feature ranking approach discussed herein, a broadcast layer 126 is provided which selects and/or filters the input features 102 before they propagate through the separate, parallel branches 120 of the neural network. In one implementation (FIG. 3), the broadcast layer 126 is an element-wise multiplicative layer whose weights, w, are learned during neural network training. In accordance with the present approach, the weights w of the broadcast layer 126 reveal the relevance of feature 102 for different tasks 122, i.e., the greater the weight, the greater the relevance of a feature to a given task, which may facilitate subsequent selection of one or more features as being relevant to a given task or application.

By way of explanation, let the input samples {X} be represented by N features 102. Let W be the collection of weights of the feature weighting layer (i.e., broadcast layer 126). For a K-task learning problem, W has N*K weights, where for every task, N scaling coefficients $W_k$ are learned.

One benefit of this approach is it allows joint discovery of task-specific features 112 (i.e., those features contributing to a specific task or a limited number of tasks) and shared or common features 110 (i.e., those features contributing to all or most tasks) across multiple tasks 122. The identified features ranked in this manner may then be selected from for a given application or task. In one implementation (FIG. 4), the broadcast layer 126 weights for every task $W_k$ is a linear addition of common and $k^{th}$ task specific features as shown in equation (1):

$$W_k = W_s + W_k^e \quad (1)$$

where $W_s$ corresponds to the weights of the shared features across tasks 122 while $W_k^e$ are the weights of features exclusive to task K.

To find a reduced set of relevant features 102, sparsity may be imposed on $W_k$ as shown in equation (2), where one enforces an L1 norm to be D-sparse, where D<<N:

$$|W_k| \leq D \quad (2)$$

Two approaches are contemplated for separating out common features 110 across tasks 122.

In a first approach, denoted low-rank recovery, the weights $W_k$ are arranged as column vectors in W. As may be seen from equations (1) and (2), the resulting matrix W should be a low-rank matrix. Shared features weights $W_s$ may be recovered as the common low-rank part of W. This can be achieved using conventional low-rank recovery techniques.

Alternatively, orthogonalization may be used as an explicit way of achieving feature separation. (K+1)*N weights may be learned for $W=\{W_s, \{W_k^e\}\}$, where the additional N are for the shared features. The contribution of $W_s$ is used for every task using equation (1), as shown in FIG. 4. Orthogonality is enforced between k pairs of weights: $\{W_s, W_k^e\}$. It is believed that the shared features are not task-exclusive features or vice-versa. Note that orthogonality can also be enforced between pair of tasks $\{W_i^e, W_j^e\}$. This may be accomplished by including a $W_i^e \cdot W_j^e$ (i.e., dot product) term in the loss function.

Relevance (i.e., importance) of a specific feature n to task k may be inferred from the absolute value of the weight $W_k(n)$, where:

$$\text{Importance } (n,k) = \text{abs}(W_k(n)) \quad (3)$$

With this in mind Table 1 shows a table of weights vectors after training:

TABLE 1

| Features | $W_S$ | $W_i$ | ... | $W_j$ |
| --- | --- | --- | --- | --- |
| Feature 1 | 1.0 | 0.0 | ... | 0.0 |
| Feature 2 | 1.0 | 0.0 | ... | 0.0 |
| Feature 3 | 1.0 | 0.0 | ... | 0.0 |
| Feature 4 | 0.0 | 1.0 | ... | 0.0 |
| Feature 5 | 0.0 | 1.0 | ... | 0.0 |
| Feature 6 | 0.0 | 0.5 | ... | 0.5 |
| Feature 7 | 0.0 | 0.0 | ... | 1.0 |
| Feature 8 | 0.0 | 0.0 | ... | 1.0 |
| Feature 9 | 0.0 | 0.0 | ... | 0.0 |
| Feature 10 | 0.0 | 0.0 | ... | 0.0 |
| ... | ... | ... | ... | ... |

The trained weights may not be exactly 0 or 1 as generally shown, but are expected to be close to 0 or 1. In some instances where a low value is observed, a 0 value may be forced to enhance differences. In spite of sparsity constraints, some weights might assume values close to 0.5, as shown in the $W_j$ column. From the weights, features can be broadly classified based on the roles played by them in teaching the multi-task network into: common features (e.g., high $W_S$ values, such as $W_S$ weights of 1), task specific features (e.g., high $W_{i, j}$, ... values, such as weights of 1), and/or redundant features (i.e., noise). By this classification each of these features is expected to be orthogonal to each other. The orthogonality constraint is added to the loss function with the sparsity constraint. In the example shown in Table 1, Features 1-3 may be deemed common or shared features as they have a common feature weight $W_S=1$; Features 4 and 5 are task specific features for task i, with respective weights of $W_i=1$); Features 7 and 8 are task specific features for task j, with respective weights of $W_j=1$); Features 9 and 10 are noise, with no non-zero weight for any specific task or common to all tasks. In the case of Feature 6, in this example the weights of $W_i$ and $W_j$ are both implicated evenly (e.g., weights of 0.5), suggesting this feature is equally involved in both tasks. In this instance, Feature 6 is not a common or shared feature that contributes to all tasks, but instead contributes significantly (here equally) to only two (i.e., a limited number) of the plurality of tasks (here tasks i and j), which may provide useful insight to a commonality between these tasks.

Further, from domain knowledge, if some group of tasks are known to have similar feature base, then a similarity constraint can be posed by including a $-W_i^e \cdot W_j^e$ (i.e., negative of dot product) term in the loss function. Such domain knowledge and/or similarity constraints may be provided as a user input to guide or direct the feature ranking process. Turning to Table 2, an example is provided demonstrating tasks with feature base similarity, where for Features 4 and 5 can be seen to be similar in view of weights $W_x$ and $W_y$.

TABLE 2

| Features | $W_S$ | ... | $W_x$ | $W_y$ | ... |
| --- | --- | --- | --- | --- | --- |
| Feature 1 | 1.0 | ... | 0.0 | 0.0 | 0.0 |
| Feature 2 | 1.0 | ... | 0.0 | 0.0 | 0.0 |
| Feature 3 | 1.0 | ... | 0.0 | 0.0 | 0.0 |

TABLE 2-continued

| Features | $W_S$ | ... | $W_x$ | $W_y$ | ... |
|---|---|---|---|---|---|
| Feature 4 | 0.0 | ... | 1.0 | 1.0 | 0.0 |
| Feature 5 | 0.0 | ... | 1.0 | 1.0 | 0.0 |
| Feature 6 | 0.0 | ... | 0.0 | 0.0 | 0.0 |
| Feature 7 | 0.0 | ... | 0.0 | 0.0 | 0.0 |

With the preceding in mind, the present approach may be used interpret deep neural networks without compromising the performance of the networks. Such benefits may improve adoption of deep learning algorithms over classical machine learning algorithms for problems where interpretability is necessary or otherwise beneficial, such as in radiology, anomaly detection, and so forth. For example, in the context of biomarker discovery, the separation of shared features 110 and task-specific features 112 in a multi-task learning framework as discussed herein is essentially biomarker discovery and may facilitate prognosis, diagnosis and treatment of diseases.

In addition, the present approach may be useful for building or improving the efficiency of lean models using the identified subset of features for every task, which would contribute to a smaller compute and memory footprint. By way of example, based upon the identified relevant features for a given task, a model or additional neural network may be generated based only on the relevant identified features. In certain implementations, a user may provide additional input in selecting from among the identified relevant features to further select which features are used in constructing the limited model or neural network. In other implementation, all identified relevant features may be used in the limited model or neural network or a subset of the relevant features may be selected using an automated algorithm or routine, such as automatically selecting a subset of relevant features based upon the largest weights, based upon reducing or limiting covariance among the selected features, and so forth. By way of example, a typical ECG interpretation consists of predicting from potentially ~1,000 different diagnosis codes. Building neural nets with present multi-task feature ranking nets with sharing factor 'M' directly leads to a model which is 'M' times leaner.

Further multi-task learning problems tend to suffer from issues like class imbalance, diversity in samples, and so forth which may lead to unstable, unreliable networks. The reduction in parameters that is possible using feature ranking as discussed herein can improve stability of the neural networks, with the broadcast layer 126 acting as a learned regularization.

data (i.e., a single task). Several measurements (interchangeably called features in machine learning parlance) were made on a raw ECG waveform used as the input while the presence or absence of IMI was considered as the output. As discussed herein, the broadcast layer 126 discussed above was used to identify the key features which contributed to the prediction. These features were then correlated with clinical features which are known as contributing features to the presence of IMI.

The study dataset consisted of 500,000 ECG cases with features 102 extracted from twelve leads. Some of these features included: Q-wave duration, Q-wave amplitude, Q-wave area, Q to R amplitude ratio, QRS axis, and T-wave inversion.

A list of 72 features was used to predict the presence of IMI. A multilayer perceptron (MLP) neural network was trained to predict the presence of IMI. Three hidden layers 58 were used, each network consisting of 200 neurons each. Using this network, an accuracy of 96% was achieved. The sensitivity of the network was 79% while the specificity was 97%. In accordance with the present approach employing a broadcast layer 126, a list of features was extracted along with an importance or relevance score (Equation (3)) for the given task.

Figure 5:
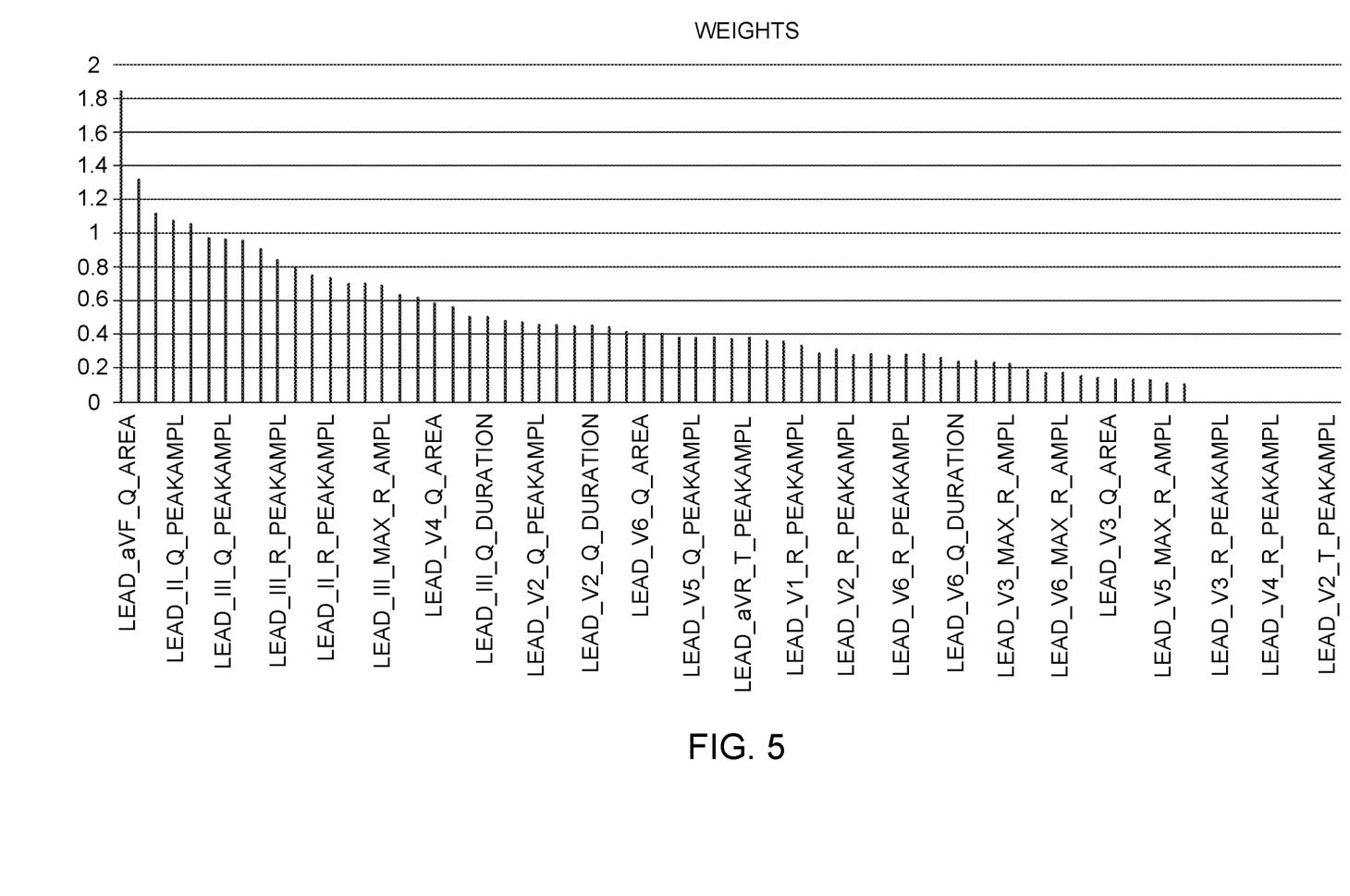
FIG. 5 depicts a chart ranking the features by their importance for a non-limiting example implementation based on IMI detection, in accordance with aspects of the present disclosure.

Based on this study, FIG. 5 is a chart ranking the features by their importance for IMI detection as defined by Equation (3). The selected features were found to correlate with features which are known to be clinically important in the prediction of IMI. It should be noted that diagnosis of IMI involves detecting abnormal Q-waves from specific leads (i.e., aVF, II) and this is captured by the ranking of the corresponding Q-wave morphology features in FIG. 5.

Further, an additional experiment was conducted using approximately half the number of initial features (35 features in this instance) to further test the feature importance results. The resultant network using a restricted number of features provided a comparable result to the previous experiment.

The present approach was further tested with respect to multiple tasks. Specifically, experiments were performed on two important, related ECG diagnoses: anterior myocardial infarction (AMI) and inferior myocardial infarction (IMI). The datasets and features used were same as in the preceding experiments. Orthogonality constraints were implemented as part of the feature ranking nets along with the constraints in Equations (1) and (2). Features were sorted according to Equation (3) and three types of features were listed: 1) shared features, 2) features specific to IMI, and 3) features specific to AMI, as shown in Table 3:

TABLE 3

| S. No | Shared Features | Features specific to IMI | Features specific to AMI |
|---|---|---|---|
| 1 | Lead_aVF_Q_Duration | Lead_aVF_Q_PeakAmpl | Lead_V1_Q_Area |
| 2 | Lead_aVR_Q_Duration | Lead_III_Q_PeakAmpl | Lead_aVL_Q_Duration |
| 3 | Lead_V2_T_PeakAmpl | Lead_aVF_Q_Area | Lead_V1_Q_Duration |
| 4 | Lead_I_T_PeakAmpl | Lead_II_Q_Duration | Lead_III_Q_Duration |
| 5 | Lead_II_Max_R_Ampl | Lead_aVL_Max_R_Ampl | Lead_V5_Max_R_Ampl |
| 6 | Lead_V4_R_PeakAmpl | Lead_III_Q_Area | Lead_V4_Max_R_Ampl |
| 7 | Lead_aVR_Q_PeakAmpl | Lead_II_Q_PeakAmpl | Lead_aVR_Q_Area |

The following example provides a real world illustration of the use and benefit of the present approach. In this example, the feature ranking approach discussed herein was applied to the problem of diagnosing the presence of inferior myocardial infarction (IMI) from electrocardiogram (ECG)

Strikingly, features related to Q-wave morphology appear as relevant features to both the tasks as these are Q-wave abnormalities. Features identified as specific to IMI conform to what was observed on the prior experiment. Features identified as specific to AMI correspond to the anterior leads.

Finally, the shared features of Q Duration have proven to be relevant as noted in ECG literature. Thus, the features identified for the two tasks appear to be clinically reasonable.

While the preceding example relate to ECG, as previously noted, the present approach is not limited to such a context, or to medical contexts in general. That is, the present approach is generic and is not only limited to ECG diagnosis or biomarker problems but may also be applied to problems such as neuro analytics or to non-healthcare applications.

Figure 6:
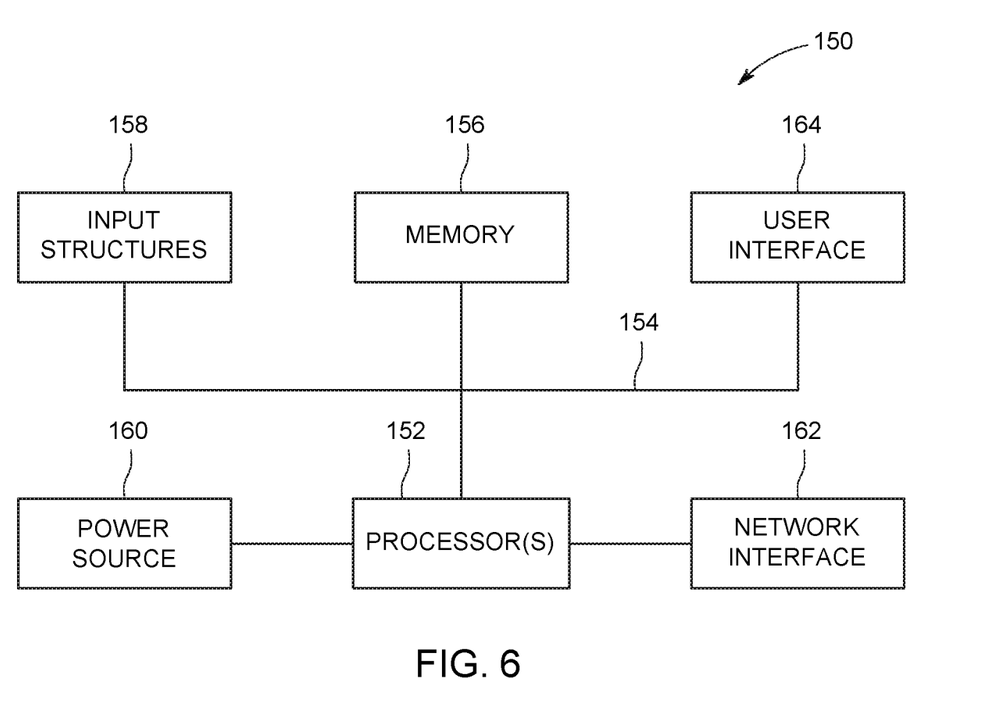
FIG. 6 is a block diagram of a computing device capable of implementing the present approach, in accordance with aspects of the present disclosure.

As will be appreciated some or all of the approach discussed herein related to feature ranking using trained deep neural networks may be performed or otherwise implemented using a processor-based system such as shown in FIG. 6 or several such systems in communication with one another. Such a system may include some or all of the computer components depicted in FIG. 6. FIG. 6 generally illustrates a block diagram of example components of a computing device 150 and their potential interconnections or communication paths, such as along one or more busses. As used herein, a computing device 150 may be implemented as one or more computing systems including laptop, notebook, desktop, tablet, or workstation computers, as well as server type devices or portable, communication type devices, and/or other suitable computing devices.

As illustrated, the computing device 150 may include various hardware components, such as one or more processors 152, one or more busses 154, memory 156, input structures 158, a power source 160, a network interface 162, a user interface 164, and/or other computer components useful in performing the functions described herein.

The one or more processors 152 are, in certain implementations, microprocessors configured to execute instructions stored in the memory 156 or other accessible locations. Alternatively, the one or more processors 152 may be implemented as application-specific integrated circuits (ASICs), field-programmable gate arrays (FPGAs), and/or other devices designed to perform functions discussed herein in a dedicated manner. As will be appreciated, multiple processors 152 or processing components may be used to perform functions discussed herein in a distributed or parallel manner.

The memory 156 may encompass any tangible, non-transitory medium for storing data or executable routines, including volatile memory, non-volatile memory, or any combination thereof. Although shown for convenience as a single block in FIG. 8, the memory 156 may actually encompass various discrete media in the same or different physical locations. The one or more processors 152 may access data in the memory 156 via one or more busses 154.

The input structures 158 are used to allow a user to input data and/or commands to the device 150 and may include mice, touchpads, touchscreens, keyboards, and so forth. The power source 160 can be any suitable source for providing power to the various components of the computing device 150, including line and battery power. In the depicted example, the device 100 includes a network interface 162. Such a network interface 162 may allow communication with other devices on a network using one or more communication protocols. In the depicted example, the device 100 includes a user interface 114, such as a display configured to display images or date provided by the one or more processors 152.

Technical effects of the invention include the ranking of features using deep neural networks in a multi-task and/or multi-label setting. Features may be identified that are task-specific as well as features that are shared across multiple tasks. In addition to facilitating interpretability, the selected subset of features can be used to make efficient models leading to better stability & regularization along with reduced compute and memory usage, leading to more efficient implementations.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A feature ranking neural network, comprising:
   an input layer;
   a broadcast layer encoding a plurality of weights, wherein the plurality of weights comprise a task specific weight for each task of a plurality of tasks for which the neural network is trained;
   two or more separate and parallel branches of the feature ranking neural network, wherein the branches are configured to receive a set of filtered inputs from the broadcast layer based on the weights encoded by the broadcast layer, wherein each branch corresponds to a different task, and wherein an orthogonalization technique is applied to the plurality of weights to identify at least one feature shared between the two or more separate and parallel branches, and wherein the set of filtered inputs represent electrocardiogram data values; and
   an output layer downstream from the branches, wherein the output layer is configured to provide an output of the feature ranking neural network, wherein the output indicates a presence or an absence of an inferior myocardial infarction.

2. The neural network of claim 1, wherein the weights of the broadcast layer filter input features provided to the input layer in a task-specific manner to the branches of the feature ranking neural network.

3. The neural network of claim 1, wherein the plurality of weights further includes a common weight attributable to each task for which the neural network is trained, and wherein the neural network is to indicate the presence of the inferior myocardial infarction in response to detecting one or more abnormal Q-waves from one or more leads that detect the electrocardiogram data values.

4. The neural network of claim 1, wherein each weight of the plurality of weights is approximately zero or approximately one.

5. The neural network of claim 1, wherein the two or more branches of the feature ranking neural network each comprise a plurality of hidden layers.

6. The neural network of claim 1, wherein the plurality of weights of the broadcast layer is learned by training the feature ranking neural network.

7. A feature ranking method, comprising:
   providing as a training data set a plurality of input samples to an input layer of a neural network, wherein each input sample is characterized by one or more features, wherein the neural network comprises a plurality of layers, and wherein one of the plurality of layers is a broadcast layer comprising a respective weight for each task of a plurality of tasks;

processing the input samples to train the respective weight for each task for each of the one or more features, and wherein the input samples represent electrocardiogram data values; and for one or more tasks of the plurality of tasks, identifying one or more features as being relevant to a respective task based on the respective weights of the one or more features with respect to the respective tasks, wherein an orthogonalization technique is applied to the respective weights to identify at least one feature shared between at least two of the plurality of layers, wherein an output based on the one or more features indicates a presence or an absence of an inferior myocardial infarction.

8. The feature ranking method of claim 7, wherein different tasks are characterized by different sets of identified features.

9. The feature ranking method of claim 7, wherein processing the input samples to train the respective weight for each task for each of the one or more features further comprises training a common weight shared by the one or more features across the plurality of tasks.

10. The feature ranking method of claim 9, wherein the common weight is provided as part of the output of the feature ranking method.

11. The feature ranking method of claim 7, wherein the broadcast layer filters the one or more features in a task-specific manner.

12. The feature ranking method of claim 7, wherein the broadcast layer filters the one or more features to limit propagation of the one or more features to a plurality of parallel branches of the neural network downstream from the broadcast layer.

13. The neural network training method of claim 7, further comprising:

receiving a user input further limiting the one or more features identified as being relevant to the respective task.

14. The neural network training method of claim 7, further comprising:

imposing a sparsity constraint on the respective weights for each task for each of the one or more features.

15. The neural network training method of claim 7, further comprising:

based on a user input, imposing a similarity constraint for the respective weights associated with two or more tasks having a similar feature base.

16. The neural network training method of claim 7, wherein the one or more features comprise one or more biomarkers of interest, a targeted therapy or treatment, an electrocardiogram diagnosis, or a neuro-analytic treatment or diagnosis.

17. A method for generating a reduced feature set model, comprising:

acquiring one or more weights associated with a broadcast layer of a trained neural network, wherein each weight is associated with a respective feature and task combination, wherein the one or more weights correspond to input samples representing electrocardiogram data values;

identifying one or more task-specific features for a given task based on the weights; and generating a model based on the one or more task-specific features, wherein the one or more task-specific features is a subset of a larger feature set for which the trained neural network was trained, and wherein an orthogonalization technique is applied to the one or more weights to identify at least one feature shared between the two or more layers of the trained neural network, and wherein an output from the model indicates a presence or an absence of an inferior myocardial infarction.

18. The method of claim 17, wherein the model comprises a task-specific neural network.

19. The method of claim 17, wherein the one or more task specific features are identified based on user inputs in addition to the weights.

20. The method of claim 17, further comprising using the model to evaluate additional observations related to the task based on observed values of the one or more task-specific features.

* * * * *